(12) United States Patent
Hsieh et al.

(10) Patent No.: US 7,344,306 B2
(45) Date of Patent: Mar. 18, 2008

(54) SYSTEMS AND METHODS FOR COMPENSATING FOR TABLE SAG

(75) Inventors: Jiang Hsieh, Brookfield, WI (US); Richard Zane DeLoach, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/172,067

(22) Filed: Jun. 30, 2005

(65) Prior Publication Data

US 2007/0003020 A1    Jan. 4, 2007

(51) Int. Cl.
*G01D 18/00* (2006.01)

(52) U.S. Cl. .......................................... 378/207; 378/20

(58) Field of Classification Search ................ 378/208, 378/209, 205, 151, 177, 4–20, 207; 5/601; 600/415
See application file for complete search history.

(56) References Cited

U.S. PATENT DOCUMENTS

| | | | |
|---|---|---|---|
| 5,848,114 A | 12/1998 | Kawai et al. | |
| 5,907,593 A | 5/1999 | Hsieh et al. | |
| 5,970,112 A | 10/1999 | Hsieh | |
| 6,269,501 B1 * | 8/2001 | Li et al. | ........................ 5/601 |
| 6,332,013 B1 | 12/2001 | Hsieh | |
| 6,529,764 B1 | 3/2003 | Kato et al. | |
| 6,628,984 B2 | 9/2003 | Weinberg | |
| 6,678,346 B2 | 1/2004 | Hsieh | |
| 6,728,331 B1 | 4/2004 | McDaniel et al. | |
| 7,020,315 B2 * | 3/2006 | Vaisburd et al. | ............ 382/131 |
| 2004/0101087 A1 | 5/2004 | Hsieh | |
| 2006/0093093 A1 * | 5/2006 | Chao et al. | ................. 378/207 |

* cited by examiner

*Primary Examiner*—Hoon Song
(74) *Attorney, Agent, or Firm*—Armstrong Teasdale LLP

(57) ABSTRACT

A method for compensating for table sag is described. The method includes receiving a first dimension of a table, scanning a patient placed on the table to obtain a first data set, generating an image of the table by performing the scanning with the patient on the table, and determining a difference between the first dimension and a second dimension of the table in the image.

18 Claims, 7 Drawing Sheets

SYSTEMS AND METHODS FOR COMPENSATING FOR TABLE SAG

BACKGROUND OF THE INVENTION

This invention relates generally to medical imaging systems and more particularly to systems and methods for compensating for table sag.

In at least some computed tomography (CT) imaging system configurations, an x-ray source projects a fan-shaped x-ray beam which is collimated to lie within an X–Y plane of a Cartesian coordinate system and generally referred to as an "imaging plane". The x-ray source is coupled to a gantry 20 shown in FIG. 1. The x-ray beam passes through an object, such as a patient, being imaged. The object is located on a table 22 that is slidably located on a base 24. The x-ray beam, after being attenuated by the object, becomes an attenuated beam that impinges upon a detector array. Intensity of the attenuated beam received at the detector array is dependent upon the attenuation of the x-ray beam received by the object. Each detector element of the detector array produces a separate electrical signal that is a measurement of the attenuation at a location of the detector array. The attenuation measurements from all the elements of the detector array are acquired separately to produce a transmission profile.

The x-ray source and the detector array are rotated with gantry 20 within the imaging plane and around the object to be imaged, so an angle at which the x-ray beam intersects the object constantly changes. The x-ray source typically includes an x-ray tube, which emits the x-ray beam at a focal spot. A detector element of the detector array typically includes a collimator for collimating attenuated beams received at the detector array, a scintillator adjacent the collimator, and a photodetector adjacent to the scintillator. A group of x-ray attenuation measurements or projection data from the detector array at one gantry angle is referred to as a "view". A "scan" of the object includes a set of views made at different gantry angles, or view angles, during one revolution of the x-ray source and the detector array.

Although a design of table 22 is capable of providing required accuracy in a z direction parallel to a z axis under heavy loading conditions, table 22 does not maintain a rigidity to provide a location accuracy in a y direction parallel to a y axis. Lack of the rigidity generates a table sag 26. Table sag 26 occurs when table 22 is not fully retracted away from gantry 20 in the z direction. Table 22 is fully retracted when table 22 cannot be retracted further away from gantry 20 in the z-direction. Table sag 26 occurs when table 22 is extended towards gantry 20 in the z direction. Table 22 is fully extended when table 22 cannot be extended further toward gantry 20 in the z direction.

An effect of table sag 26 is that anatomies of the object scanned with table 22 extended is shifted downward as compared to the anatomies that are scanned with table 22 retracted. In radiotherapy (RT) or alternatively positron emission tomography (PET) applications, a registration of an anatomy of the object is important. For example, in RT applications, a radiation treatment planning is performed by identifying a tumor location of a tumor in images generated by using one of the CT imaging system configurations and adjusting a radiation beam appropriately so that an area of the object on which the tumor is located is exposed to the beam and no other areas of the object are exposed. When table sag 26 occurs, however, the tumor location in the images can be several millimeters away from the area of the object in which the tumor is located. Table sag 26, therefore, leads to suboptimal treatment of the object.

FIG. 2 shows an embodiment of a plurality of images 50 and 52 generated by scanning a set of phantoms at two table locations. A first of the two table locations corresponds to a table 54 fully retracted. A second of the two table locations corresponds to table 54 extended out by an amount, such as 1090 millimeters. Sizes of the phantoms placed on table 54 correspond roughly to a small size body. Both images 50 and 52 are reconstructed with the same field of view. Ideally, the two table locations in both images 50 and 52 should be identical. However, because of table sag, table 54 in image 52 is lower than table 54 in image 50, as shown by a discontinuity 56 of table 54 at a boundary 58 between images 50 and 52. Numerical measurement indicates that table 54 in image 52 is shifted by a perpendicular distance of 4.5 millimeters compared to table 54 in image 50. Under heavier loading, table sag 26 can be expected as much as 6 millimeters.

BRIEF DESCRIPTION OF THE INVENTION

In one aspect, a method for compensating for table sag is described. The method includes receiving a first dimension of a table, scanning a patient placed on the table to obtain a first data set, generating an image of the table by performing the scanning with the patient on the table, and determining a difference between the first dimension and a second dimension of the table in the image.

In another, an imaging system is described. The imaging system includes a source configured to generate energy, a table, a detector configured to detect the energy, and a processor. The processor is configured to receive a first dimension of the table, control the source and the detector to scan a patient placed on the table to obtain a first data set, generate an image of the table by controlling the source and the detector to scan with the patient on the table, and determine a difference between the first dimension and a second dimension of the table in the image.

In yet another aspect, a processor is described. The processor is configured to receive a first dimension of a table, control a source and a detector to scan a patient placed on the table to obtain a first data set, generate an image of the table by controlling the source and the detector to scan with the patient on the table, and determine a difference between the first dimension and a second dimension of the table in the image.

DETAILED DESCRIPTION OF THE INVENTION

Figure 3:
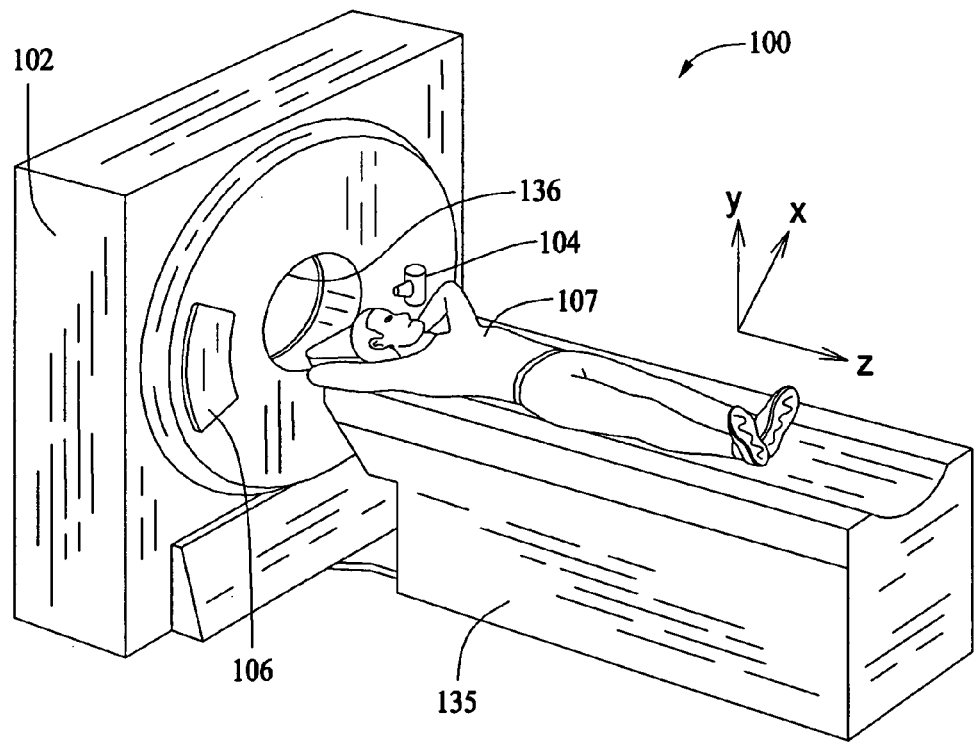
FIG. 3 is an isometric view of an embodiment of a computed tomography (CT) imaging system in which a method for compensating for table sag is implemented.
Figure 4:
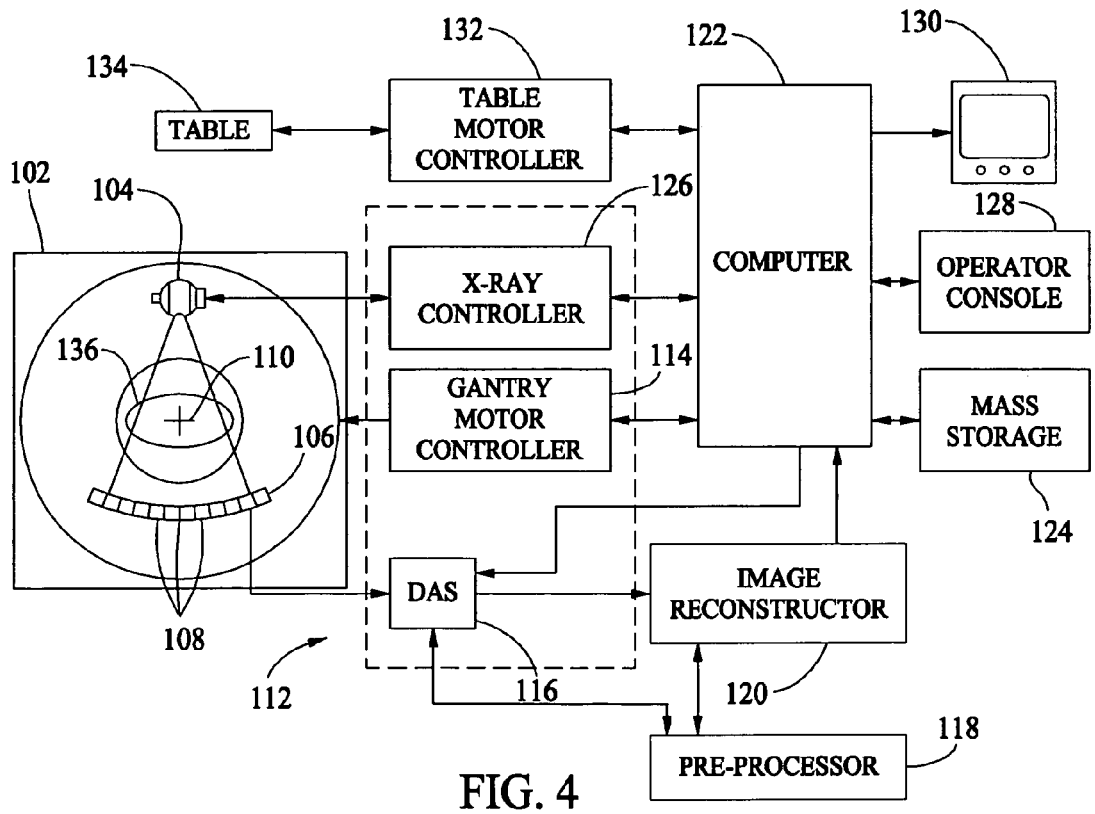
FIG. 4 is a block diagram of the computed tomography system of FIG. 3.

Referring to FIGS. 3 and 4, a computed tomography (CT) imaging system 100 is shown as including a gantry 102. CT system 100 is a "third generation" CT system. In an alternative embodiment, CT system 100 may be an energy integrating, a photon counting (PC), or a photon energy discriminating (ED) CT detector system. Gantry 102 has an x-ray source 104 that projects a beam of x-rays toward a detector array 106. The x-rays pass through an object 107, such as a patient, to generate attenuated x-rays. Detector array 106 is formed by a plurality of detector elements 108 which together sense the attenuated x-rays. In an alternative embodiment, each detector element 108 of detector array 106 may be a photon energy integrating detector, a photon counting, or a photon energy discriminating detector. Each detector element 108 produces an electrical signal that represents an intensity of the attenuated x-rays. During a scan to acquire projection data, gantry 102 and components mounted on gantry 102 rotate about a center of rotation 110.

Rotation of a gantry 102 and an operation of x-ray source 104 are governed by a control mechanism 112 of CT system 100. Control mechanism 112 includes an x-ray controller 126 that provides power and timing signals to x-ray source 104, a gantry motor controller 114 that controls a rotational speed and position of gantry 102. A data acquisition system (DAS) 116 in control mechanism 112 samples and digitizes the projection data from detector elements 108 and converts the projection data to sampled and digitized projection data for subsequent processing.

Pre-processor 118 receives the sampled and digitized projection data from DAS 116 to pre-process the sampled and digitized projection data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 118 pre-processes the sampled and digitized projection data to generate pre-processed projection data.

An image reconstructor 120 receives the pre-processed projection data from pre-processor 118 and performs image reconstruction, such as filtered backprojection (FBP), to generate a reconstructed image. The reconstructed image is applied as an input to a computer 122 which stores the reconstructed image in a mass storage device 124. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. An x-ray controller 126 adjusts a tube current within x-ray source 104 based on a quality of the reconstructed image.

Figure 1:
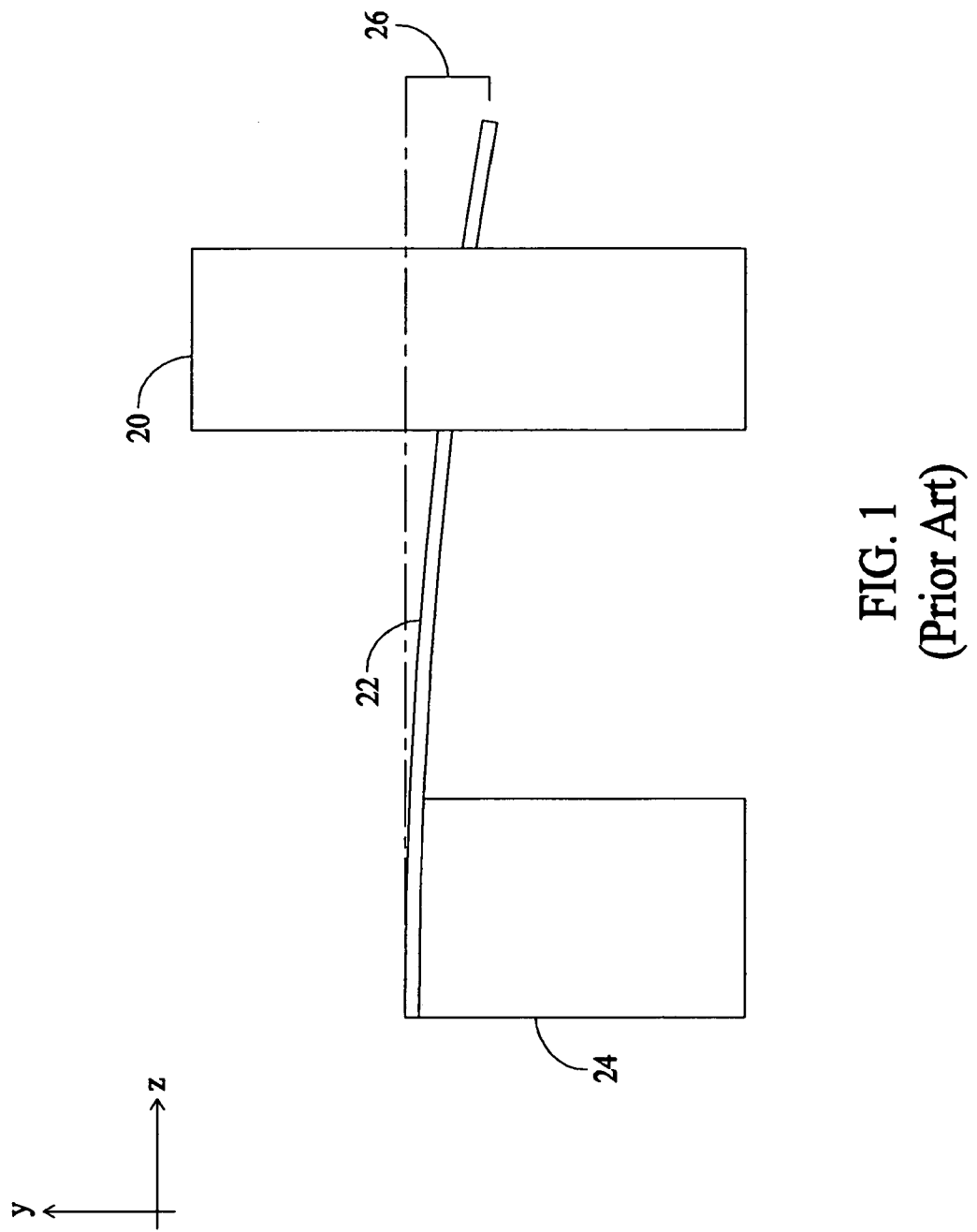
FIG. 1 is a block diagram of an embodiment of an imaging system illustrating table sag.

Computer 122 also receives commands and scanning parameters from a user, such as an operator, via a console 128 that has a user interface device. A cathode ray tube display 130 allows a user, such as an operator, to observe the reconstructed image and other data from computer 122. The commands and scanning parameters are used by computer 122 to provide control signals and information to DAS 116, x-ray controller 126, and gantry motor controller 114. In addition, computer 122 operates a table motor controller 132 which controls a motorized table 134 to position object 107 within gantry 102. Particularly, table motor controller 132 adjusts table 134 to move portions of object 107 and center object 107 in a gantry opening 136. Table 134 is located on a base 135, which is an example of base 24 (FIG. 1). Tables 22 and 54 (FIGS. 1 and 2) are examples of table 134.

In an alternative embodiment, a high frequency electromagnetic energy projection source configured to project high frequency electromagnetic energy toward object 107 may be used instead of x-ray source 104. A detector array disposed within a gantry and configured to detect the high frequency electromagnetic energy may also be used instead of detector array 106.

In another alternative embodiment, a fourth generation CT system similar to CT system 100 is used except that in the fourth generation CT system, detector array 106 is replaced by a full-ring stationary detector and the full-ring stationary detector includes detector elements corrected to provide uniform responses to an x-ray beam. In yet another alternative embodiment, a CT system similar to CT system 100 is used except that x-ray source 104 is replaced by a stationary x-ray source and detector array 106 is replaced by a stationary detector in the CT similar to CT system 100.

Computer 122 controls CT system 100 to perform a scout scan of object 107 and scout data is collected from the scout scan. In a scout scan, x-ray source 104 and detector array 106 remain stationary throughout the scout scan. As an example, x-ray source 104 is located at an angle of 90 degrees, which is at 3 o'clock position or alternatively at 9 o'clock position, from a y axis. Detector array 106 is located at an angle of 180 degrees from x-ray source 104. Object 107 is indexed at a constant speed while the x-rays are transmitted from x-ray source 104. Table motor controller 132 moves table 134 in a z-direction parallel to a z axis perpendicular to an x axis. The scout data is collected by detector array 106 and pre-processor 118 pre-processes the scout data to generate pre-processed scout data. Computer 122 receives the pre-processed scout data and applies computer enhancement techniques to produce a two-dimensional scout image with similar appearance as a conventional radiograph. Based on the scout image, the user can determine anatomical regions of object 107 for subsequent CT scans. As used herein, the terms scout scan and scout data broadly refers to all data acquisitions and data acquired where gantry 102 is stationary and table 134 is moved including, for example, but not limited to, CT scout scans as well as digitally reconstructed radiograph (DRR) acquisitions typically employed in radiation treatment (RT) planning.

Figure 5:
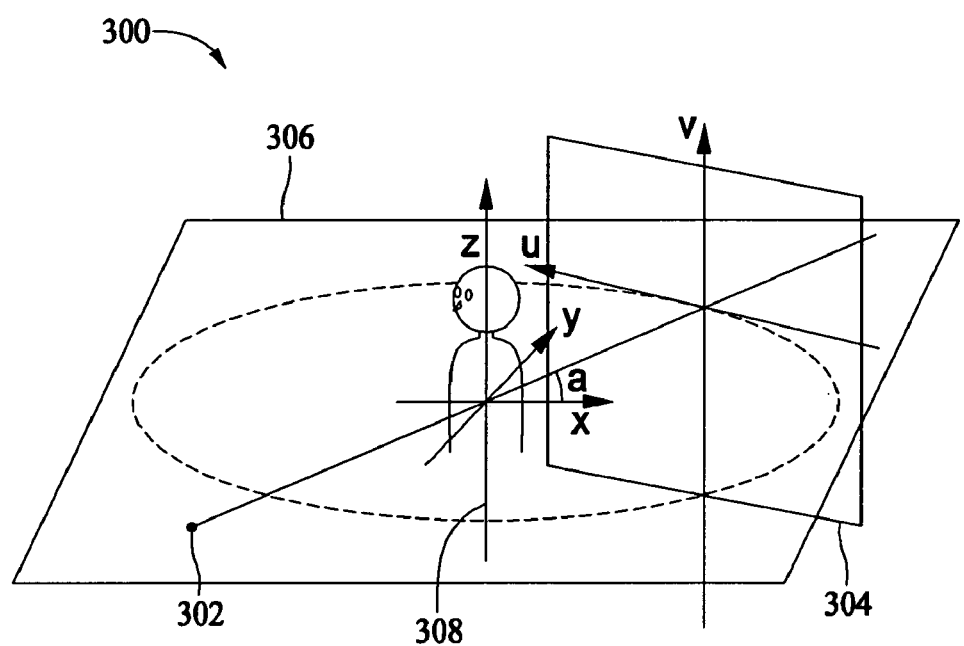
FIG. 5 shows an embodiment of a CT measuring system showing a relationship between coordinates in a projection domain and coordinates in a reconstruction domain.

FIG. 5 illustrates an embodiment of a CT measuring system 300. CT measuring system 300 includes an x-ray focal spot 302 at which x-ray source 104 is located. A projection plane 304 is a virtual two-dimensional plane which is positioned instead of a two-dimensional detector formed when detector array 106 is flattened to lie in a single plane. In an alternative embodiment, projection plane 304 is curved for curved detector array 106. A midplane 306 is a plane of rotation of x-ray focal spot 302 when the spot turns around an axis of rotation 308. Midplane 306 is a plane of rotation of x-ray source 104 and detector array 106. A u-axis shows a crossing line drawn when projection plane 304 and midplane 306 cross each other. A v-axis is a projection of axis of rotation 308 on projection plane 304 and crosses perpendicularly the u-axis. A position on projection plane 304 can be expressed by uv coordinates. The x axis and the y axis cross perpendicular to each other and are provided on midplane 306. The x and y axes perpendicularly cross the z axis, which is axis 308 of rotation of gantry 102. A projection angle a is an angle between a straight line connecting x-ray focal spot 302 and a uv-origin of the uv coordinates and the x axis. Image reconstructor 120 generates the reconstructed image from the pre-processed projection data by filtered backprojection in which the pre-processed projection data is filtered, weighted, and backprojected to generate the reconstructed image. The filtered and weighted projection data is represented as q(a,u,v) and the reconstructed image is represented as f(x,y,z), where (x,y,z) are initial reconstruction co-ordinates.

Figure 6:
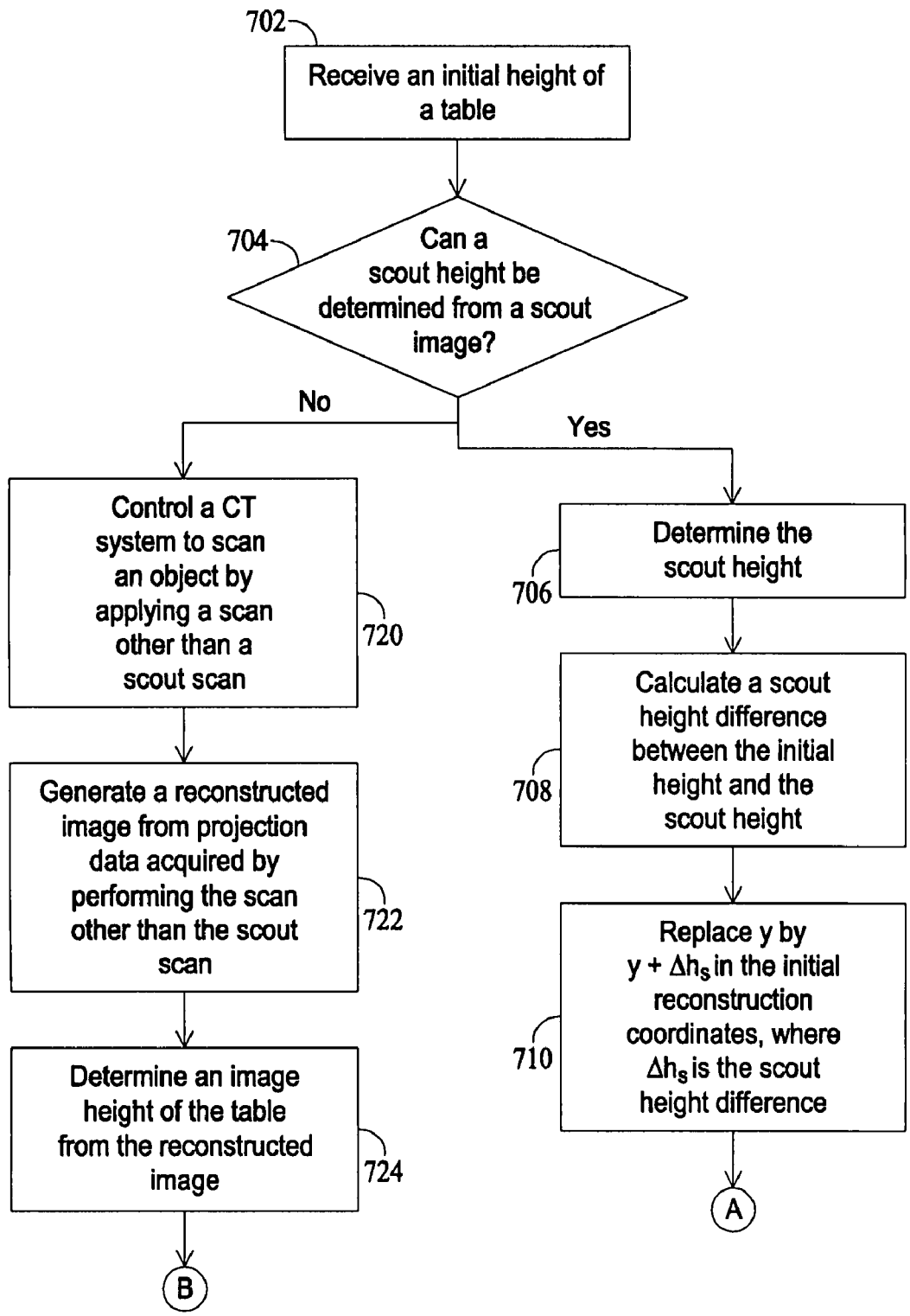
FIG. 6 is a flowchart of an embodiment of method for compensating for table sag.
Figure 7:
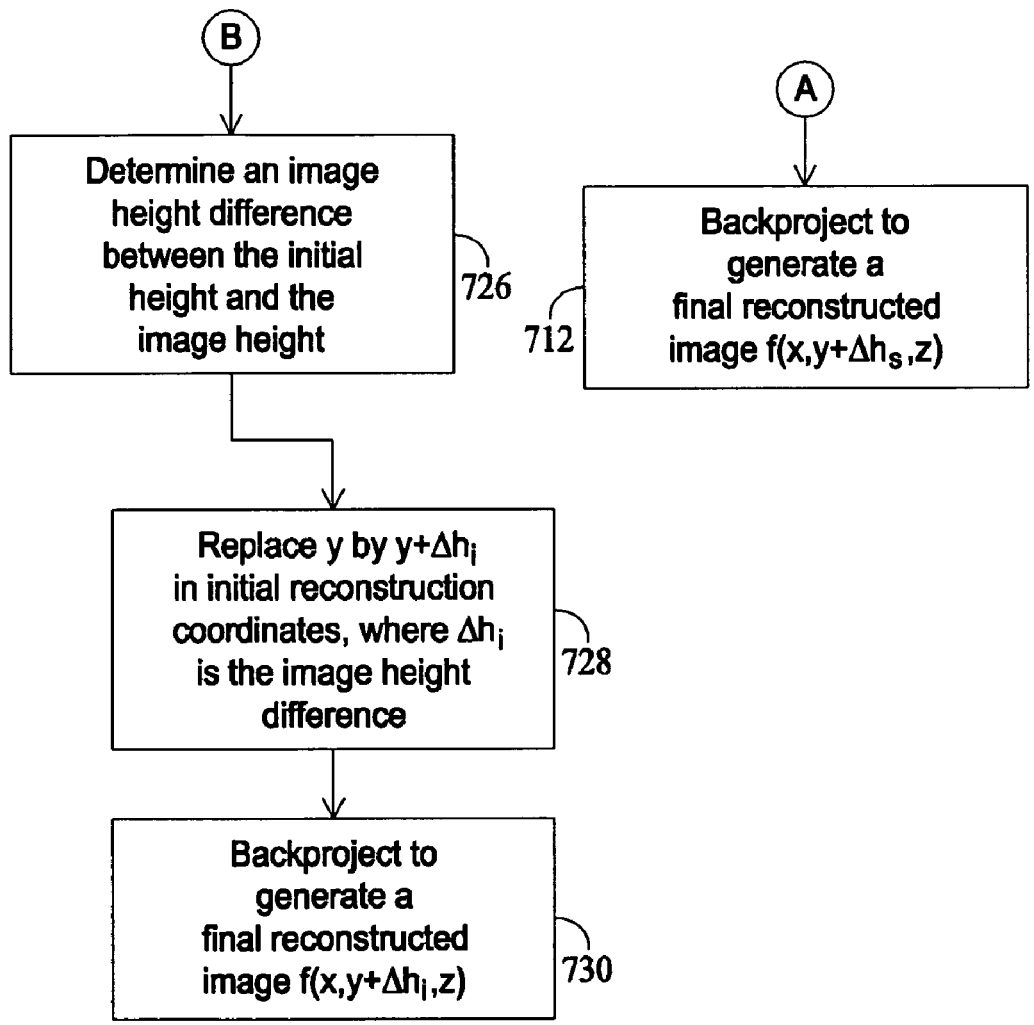
FIG. 7 is a continuation of the flowchart of FIG. 6.

FIGS. 6 and 7 are a flowchart of an embodiment of a method for compensating for table sag. Computer 122 receives 702 an initial height of table from the user. The initial height is a height measured parallel to the y axis and is a height of table measured without placing a load, such as object 107, on table 134. The initial height is a height stored in mass storage device 124 when CT system 100 is bought from a manufacturer of CT system 100 and installed at a site. The initial height is also visible on gantry 102 and on display 130 when CT system 100 is energized immediately after buying CT system 100 from the manufacturer. Computer 122 stores the initial height and determines an initial position of the initial height with respect to a reference co-ordinate system. The reference co-ordinate system has a reference origin. An example of the reference origin is a center of rotation of gantry 102. The center of rotation is fixed by computer 122 in the scout image and in the reconstructed image.

Computer 122 determines 704 whether a height of table can be determined from the scout image of table 134 with object 107 on table 134. The height of table within the scout image is referred to as a scout height. In an alternative embodiment, the user determines whether the scout height can be determined by examining the scout image. Computer 122 determines whether the scout height can be determined by searching for table 134 within the scout image. Computer 122 searches for table 134 within the scout image by searching for projection intensities within the scout image that correlate to projection intensities of table 134 within a first stored table projection profile input into computer 122 by the manufacturer. The manufacturer uses CT system 10 to generate the first stored table projection profile. The first stored table projection profile is generated by performing a scout scan of table 134 without placing object 107 on table 134. X-ray controller 126 applies the same amount of potential to x-ray source 104 when generating the scout image with a patient on table 134 and when generating the first stored table projection profile.

Computer 122 searches for projection intensities within the scout image that correlate to projection intensities within the first stored table projection profile by correlating a projection intensity at a first z location of table 134 in the scout image with a projection intensity at the first z location in the first stored table projection profile. A z location is a location on the z axis. Computer 122 searches for projection intensities within the scout image that correlate to projection intensities within the first stored table projection profile by correlating a projection intensity at a second z location of table 134 in the scout image with a projection intensity at the second z location in the first stored table projection profile. The second z location is different than the first z location.

When computer 122 determines that an amount of correlation that is the highest among a plurality of amounts of correlation between a plurality of intensities within the scout image and projection intensities within the first stored table projection profile, computer 122 compares an optimal projection intensity within the scout image that has the highest amount of correlation with an optimal projection intensity in the first stored table projection profile and determines whether a first correlation coefficient from the comparison is above a first threshold input into computer 122 by the operator via console 128. An example of the first threshold includes a value close to one, such as 0.98. Computer 122 determines that the scout height can be found from the scout image upon determining that a ratio of the optimal projection intensity within the scout image and the optimal projection intensity in the first stored table projection profile is at least equal to a predefined value and upon determining that the first correlation coefficient is greater than the first threshold. The predetermined range is value into computer 122 by the operator via console 128. An example of the predefined value includes 90 percent.

In an alternative embodiment, computer 122 searches for table 134 within the scout image by searching for projection intensities within the scout image that correlate to projection intensities within the first stored table projection profile and that are within a pre-determined perpendicular distance from each point representing the initial position on the scout image. The pre-determined perpendicular distance is a distance input by the user into computer 122. An example of the pre-determined perpendicular distance is from and including 1 centimeter to and including 2 centimeters.

In yet another alternative embodiment, computer searches for table 134 within the scout image by searching for projection intensities within the scout image that correlate to projection intensities within the first stored table projection profile and by searching for a shape of table 134 or alternatively a portion of table 134 within the scout image. Computer searches for the shape of table 134 within the scout image by comparing shapes of projection intensities of table 134 within the scout image with shapes of projection intensities within the first stored table projection profile.

In still another alternative embodiment, computer 122 searches for table 134 within the scout image by determining whether the scout height, measured parallel to the y axis, of either a top surface or a bottom surface of table 134 lies within a specific range. The specific range is input by the user via the console 128. In another alternative embodiment, computer 122 searches for table 134 within the scout image by determining whether scout height of the top surface lies within the specific range and the scout height of the bottom surface lies within a pre-determined range. In yet another alternative embodiment, computer 122 searches for table 134 within the scout image by determining whether a density of a material, such as polystyrene, between the top and bottom surfaces is within a range of densities input via console 128.

Upon determining by the user or alternatively computer 122 that the scout height can be determined from the scout image, computer 122 determines 706 the scout height. Computer 122 determines 706 the scout height by determining scout positions of table 58 at which projection intensities within the scout image correlate to projection intensities within the first stored table projection profile. Computer 122 determines the scout positions with reference to the reference origin of the reference coordinate system. Computer 122 calculates 708 a scout height difference between the initial height and the scout height.

Upon determining the scout height difference and obtaining the projection data, including additional tomographic projection data, the sampled and digitized projection data is pre-processed and forwarded to image reconstructor 120.

Upon determining the scout height difference and forwarding the pre-processed projection data to image reconstructor 120, computer 122 replaces 710 y by y+$\Delta h_s$ in the initial reconstruction coordinates (x,y,z), where x, y+$\Delta h_s$, and z are final reconstruction co-ordinates, and $\Delta h_s$ is the scout height difference. It is noted that $\Delta h_s$ is positive if the y axis has increasing numbers with an upward progression along the y axis. In an alternative embodiment, $\Delta h_s$ is negative if the y axis has decreasing numbers within an upward progression along the y axis. Image reconstructor 120 backprojects 712 to generate a final reconstructed image f(x,y+$\Delta h_s$,z) from the filtered and weighted projection data.

Upon determining by the user or alternatively computer 122 that the scout height cannot be determined from the scout image, computer 122 controls 720 CT system 100 to scan object 107 by applying a scan other than a scout scan. Example of a scan other than a scout scan includes a helical scan and an axial scan. To perform a helical scan, table controller 46 moves table parallel to the z axis in synchronization with a rotation of gantry 102, while detector array 106 collects the projection data. In an axial scan, object 107 is positioned at the same location along the z axis when gantry 102 is rotated by gantry motor controller 114 to collect the projection data. Image reconstructor 120 generates 722 the reconstructed image from the projection data acquired by performing a scan other than a scout scan.

Computer 122 determines 724 an image height of table 134 from the reconstructed image. Computer 122 determines the image height by searching for intensities located within the reconstructed image and located near the initial position of table 134. Computer 122 obtains intensities of table 134 within the reconstructed image by searching for intensities above a fixed point and within a predetermined perpendicular range from each point representing the initial position on the reconstructed image. Examples of the fixed point includes a range from and including 80 Hounsfield units to and including 100 Hounsfield units and an example of the perpendicular range includes a range from and including 1 centimeter to and including 2 centimeters. The fixed point and the predetermined perpendicular range are input into computer 122 via console 128.

In an alternative embodiment, computer 122 determines 724 the image height in a similar manner in which computer 122 determines the scout height except that instead of projection intensities of table 134 within the scout image intensities, measured in Hounsfield units, within the reconstructed image are used. For example, computer 122 searches for table 134 within the reconstructed image by searching for intensities within the reconstructed image that correlate to intensities of table 134 within a second stored table profile. The manufacturer uses CT system 10 to generate the second stored table profile. The second stored table profile is generated by performing a scan other than a scout scan of table 134 and without placing object 107 on table 134.

Computer 122 searches for intensities within the reconstructed image that correlate to intensities within the second stored table profile by correlating an intensity at a third z location of table 134 in the reconstructed image with an intensity at the third z location in the second stored table profile. Computer 122 searches for intensities within the reconstructed image that correlate to intensities within the second stored table profile by correlating an intensity at a fourth z location of table 134 in the reconstructed image with an intensity at the fourth z location in the second stored table profile. The fourth z location is different than the third z location.

When computer 122 determines that an amount of correlation that is the highest among a plurality of amounts of correlation between a plurality of intensities within the reconstructed image and intensities within the second stored table profile, computer 122 compares an optimal intensity within the reconstructed image that has the highest amount of correlation within an optimal intensity in the second stored table profile and determines whether a second correlation coefficient from the comparison is above a second threshold input into computer 122 by the operator via console 128. An example of the second threshold includes a value close to one, such as 0.98. Computer 122 determines that the image height can be found from the reconstructed image upon determining that a ratio of the optimal projection intensity within the reconstructed image and the optimal projection intensity of the second stored table profile is at least equal to the predefined value and upon determining that the second correlation coefficient is greater than the second threshold.

In yet another alternative embodiment, computer searches for table 134 within the reconstructed image by searching for intensities within the reconstructed image that correlate to intensities within the second stored table projection profile and by searching for a shape of table 134 or alternatively a portion of table 134 within the reconstructed image. Computer 122 determines 726 an image height difference between the initial height and the image height.

Upon determining 726 the image height difference, computer 122 does not control CT system 100 to re-obtain the projection data, to re-pre-process the sampled and digitized projection data, and to re-filter and re-weigh the pre-processed projection data. Computer 122 replaces 728 y, in the initial reconstruction coordinates (x,y,z) from which the image height difference is calculated, by y+$\Delta h_i$, where (x, y+$\Delta h_i$,z) are final reconstruction coordinates, and $\Delta h_i$ is the image height difference. Image reconstructor 120 backprojects 730 to generate a final reconstructed image f(x,y+$\Delta h_i$,z) from the filtered and weighted projection data.

Figure 2:
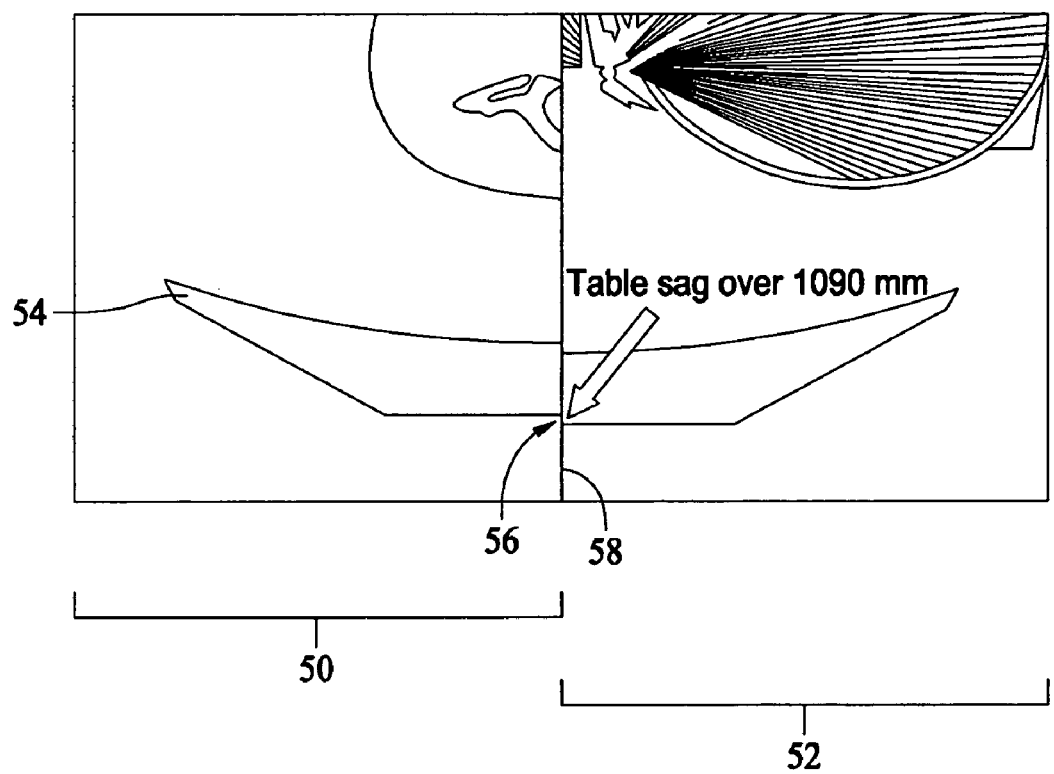
FIG. 2 shows examples of computed tomography images illustrating table sag.
Figure 8:
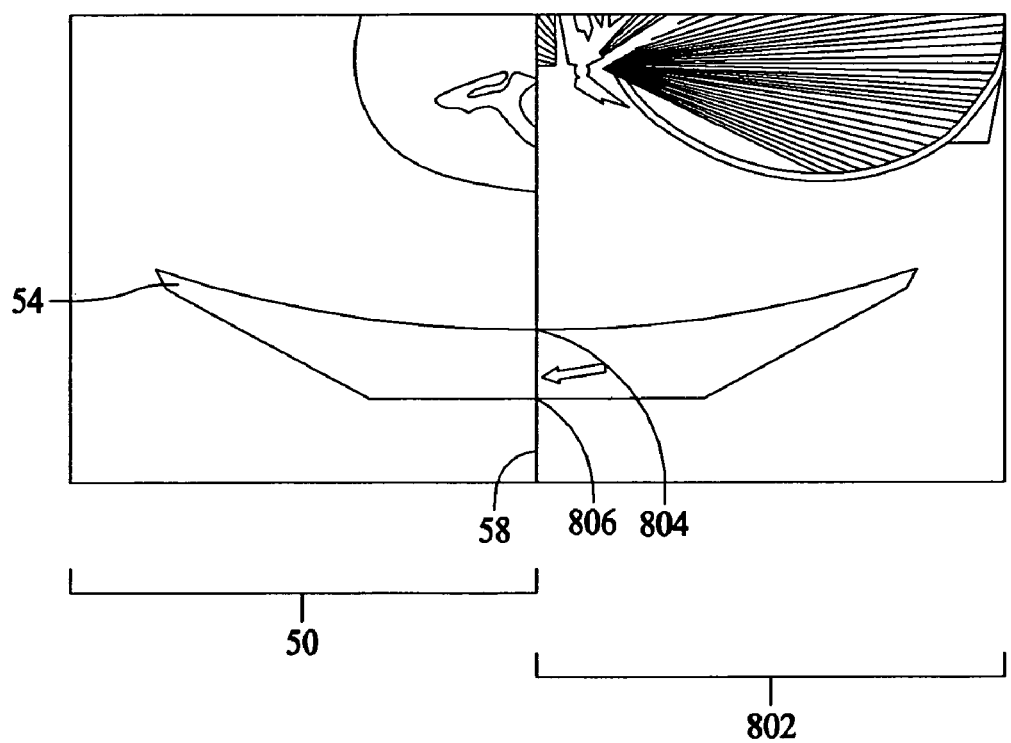
FIG. 8 shows examples of computed tomography images illustrating a compensation for table sag.

In the final reconstructed images f(x,y+$\Delta h_s$,z) and f(x,y+$\Delta h_i$,z), an artifact created by table sag is reduced. For example, as shown in FIG. 8, image 50 shows table 54 in a retracted position and an image 802 shows table 54 in a position extended by an amount, such as 1090 millimeters, from the retracted position. In images 50 and 802, table 54 is aligned at points 804 and 806 between images 50 and 802 compared to table 54 shown in images 50 and 52 (FIG. 2).

Computer 122 applies methods for compensating for table sag to the reconstructed image generated from the projection data at the reference origin, does not apply methods for compensating for table sag to additional reconstructed images generated from additional projection data located within N−1 millimeters along the z axis from the reference origin, and applies the methods for compensating for table sag to an additional reconstructed image generated from additional projection data at N millimeters along the z axis. Computer 122 fits a smooth curve between table 134 visible in one of the final reconstructed images and table 134 visible in an additional final reconstructed image N millimeters from the one of the final reconstructed images to determine additional height differences in additional reconstructed images generated from additional projection data within and including N−1 millimeters. As an example, the smooth curve is a straight line parallel to the z axis. Computer 122 substitutes ys, which are a plurality of ys, in additional initial reconstruction coordinates (x,y,z)s of additional filtered and weighted projection data from which additional reconstructed images are generated with the additional height differences, and backprojects the additional filtered and weighted projection data to generate additional final reconstructed images within and including N−1 millimeters. In an alternative embodiment, computer 122 applies methods for compensating for table sag in any number of additional reconstructed images within N−1 millimeters.

It is noted that methods for compensating for table sag apply to other imaging systems, such as, a positron emission tomography (PET) imaging system, a CT-PET imaging system, a magnetic resonance imaging (MRI) imaging system, or an ultrasound imaging system. For example, one of 712 and 726 (FIG. 7) is executed during backprojection performed in the CT-PET imaging system or alternatively in a magnetic resonance imaging (MRI) system. Examples of the CT-PET imaging system include a Discovery LS PET-CT system commercially available from General Electric™ Medical Systems, Waukesha, Wis. Another example of the CT-PET imaging system includes a Discovery ST system commercially available from General Electric™ Medical Systems.

It is also noted that methods for compensating for table sag can be applied to dimensions other than a y dimension measured along the y axis. For example, instead of obtaining the scout height difference or the image height difference, a difference between a preliminary position of table 134 measured with respect to the reference coordinate system without placing a load on table 134 and a secondary position of table 134 from the scout image or the reconstructed image is obtained. As another example, instead of replacing y by $y+\Delta h_s$ in the initial reconstruction coordinates (x,y,z) and backprojecting to generate the final reconstructed image $f(x, y+\Delta h_s, z)$, computer 122 replaces x by $x+\Delta w_s$ in the initial reconstruction coordinates and image reconstructor 120 backprojects to generate a final reconstructed image $f(x+\Delta w_s, y, z)$, where $\Delta w_s$ is a difference between the preliminary and secondary positions measured along the x axis and obtained from the scout image. As yet another example, instead of replacing y by $y+\Delta h_i$ in the initial reconstruction coordinates (x,y,z) and backprojecting to generate the final reconstructed image $f(x, y+\Delta h_i, z)$, computer 122 replaces x by $x+\Delta w_i$ in the initial reconstruction coordinates and image reconstructor 120 backprojects to generate a final reconstructed image $f(x+\Delta w_i, y, z)$, where $\Delta w_i$ is a difference between the preliminary and secondary positions measured along the x axis and obtained from the reconstructed image. As still another example, instead of replacing y by $y+\Delta h_s$ in the initial reconstruction coordinates (x,y,z) and backprojecting to generate the final reconstructed image $f(x, y+\Delta h_s, z)$, computer 122 replaces z by $z+\Delta l_s$ in the initial reconstruction coordinates and image reconstructor 120 backprojects to generate a final reconstructed image $f(x,y, z+\Delta l_s)$, where $\Delta l_s$ is a difference between the preliminary and secondary positions measured along the z axis and obtained from the scout image. As yet another example, instead of replacing y by $y+\Delta h_i$ in the initial reconstruction coordinates (x,y,z) and backprojecting to generate the final reconstructed image $f(x, y+\Delta h_i, z)$, computer 122 replaces z by $z+\Delta l_i$ in the initial reconstruction coordinates and image reconstructor 120 backprojects to generate a final reconstructed image $f(x,y,z+\Delta l_i)$ where $\Delta l_i$ is a difference between the preliminary and secondary positions measured along the z axis and obtained from the reconstructed image.

More marks are used to obtain the difference between the preliminary and secondary positions in a direction of the z axis than number of marks used to obtain the difference between the preliminary and secondary positions in a direction of the x axis or alternatively in a direction of the y axis.

Examples of the other dimensions include an x-dimension measured along the x axis and a z-dimension measured along the z axis. An example of the preliminary position includes a distance along the x axis of an edge of table 134 from the reference origin and an example of the secondary position includes a distance, obtained from the scout image or the reconstructed image, along the x axis of the edge of table from the reference origin. Another example of the preliminary position includes a distance along the z axis of an edge of table 134 from the reference origin of the reference coordinate system and an example of the secondary position includes a distance, obtained from the scout image or the reconstructed image, along the z axis of the edge of table from the reference origin. The preliminary position is visible on gantry 102 and on display 130 when CT system 100 is energized immediately after buying CT system 100 from the manufacturer.

Computer 122 determines table sag, such as the image height difference, at a point A of table 134 in the reconstructed image from image bending characteristics of table 134 visible in the reconstructed image. An example of the image bending characteristics include image height differences at a point B and a point C of table 134 visible in the reconstructed image. Points B and C may lie in a scan plane of a CT imaging system of the CT-PET imaging system and point A may lie in a scan plane of a PET imaging system of the CT-PET imaging system. A location of point A on table 134 is different than locations of points B and C of table 134, and a location of point B is different than a location of point C of table 134. Computer 122 determines the image bending characteristics by applying 702, 704, 720, 722, 724, and 726 (FIGS. 6 and 7). Computer 122 generates a polynomial, such as a cubic polynomial, representing an image relationship between the image bending characteristics and initial positions of points, such as points B and C, from the reference origin within the reconstructed image. An example of the image relationship includes $\Delta h_i = ah_i^3 + bh_i^2 + ch_i + d$, where $h_i$ is a variable representing the initial positions of points of table 134, and a, b, c, and d are constants. Computer 122 applies the image relationship to generate $\Delta h_{il}$, which is the image height difference for the point A of table 134 located at an initial position $h_l$ from the reference origin. Computer 122 inputs $h_{il}$ into the image relationship to generate $\Delta h_{il}$.

In an alternative embodiment, computer 122 determines table sag, such as the scout height difference, at point A of table 134 in the scout image from scout bending characteristics of table 134 visible in the scout image. An example of the scout bending characteristics include scout height differences at points B and C of table 134 visible in the scout image. Computer 122 determines the scout bending characteristics by applying 702, 704, 706, 708, and 710 (FIG. 7). Computer 122 generates a polynomial representing a scout relationship between the scout bending characteristics and initial positions of points, such as points B and C, from the reference origin within the scout image. An example of the scout relationship includes $\Delta h_s = ah_s^3 + bh_s^2 + ch_s + d$, where $h_s$ is a variable representing the initial positions of points of table 134 in the scout image from the reference origin. Computer 122 applies the scout relationship to generate $\Delta h_{sl}$, which is the scout height difference for the point A of table 134 located at an initial position $h_{sl}$ from the reference origin. Computer 122 inputs $h_{sl}$ into the relationship to generate $\Delta h_{sl}$.

Although the herein described methods for compensating for table sag are described in a medical setting, it is contemplated that benefits of the methods accrue to non-medical imaging systems such as systems typically employed in an industrial setting or a transportation setting, such as, for example, a baggage scanning system for an airport, other transportation centers, government buildings, or office buildings. The benefits also accrue to micro PET and CT systems which are sized to study lab animals as opposed to humans.

Technical effects of systems and methods for compensating for table sag include electronically compensating for table sag without a need to use table motor controller 132 to adjust table sag. Further technical effects of systems and methods for compensating for table sag include backprojecting an image from the same filtered and weighted projection data from which the image height difference is calculated. Additional technical effects of systems and methods for compensating for table sag include foregoing calculations of additional scout height differences and additional image height differences for compensating for table sag visible in additional reconstructed images by fitting the smooth curve. Technical effects of systems and methods for compensating for table sag include compensating for the table sag without a need to add additional hardware to CT system 100. Table sag can be reduced by placing the additional hardware, such as sensors or at least one additional support under table 134, within CT system 100. The sensors sense an amount of table sag which can be reduced. Methods for compensating for table sag compensate for the table sag without a need to add the additional hardware.

While the invention has been described in terms of various specific embodiments, those skilled in the art will recognize that the invention can be practiced with modification within the spirit and scope of the claims.

What is claimed is:

1. A method for compensating for table sag, the method comprising:
    obtaining a first data set representing a first table position of a table;
    scanning, by an energy source and a detector, a patient placed on the table to obtain a a second data set at a second table position;
    determining, by a processor operatively coupled to the detector, a difference between a first dimension of the table in the first data set and a corresponding second dimension of the table in the second data set in scanned image of the table; and
    generating, based on the determined difference, a reconstructed image.

2. A method in accordance with claim 1 wherein the scanning the patient comprises performing a scout scan of the patient.

3. A method in accordance with claim 1 wherein the scanning the patient comprises performing at least one of a helical scan and an axial scan.

4. A method in accordance with claim 1 wherein the scanning the patient comprises performing at least one of a helical scan and an axial scan if the difference cannot be obtained from an image generated from a scout scan of the patient.

5. A method in accordance with claim 1 further comprising reconstructing an image of the patient on the table by replacing the second dimension with a sum of the second dimension and the difference.

6. A method in accordance with claim 1 further comprising:
    reconstructing an image of the patient on the table by replacing the second dimension with a sum of the second dimension and the difference; and
    reconstructing an additional image from data obtained by scanning at a position displaced N units from a position at which the first set of data is obtained.

7. A method in accordance with claim 1 further comprising:
    reconstructing an image of the patient on the table by replacing the second dimension with a sum of the second dimension and the difference;
    reconstructing an additional image from data obtained by scanning at a position displaced N units from a position at which the first set of data is obtained;
    determining an additional difference between the first dimension and a third dimension of the table in the additional image; and
    reconstructing another image by replacing the third dimension with a sum of the third dimension and the additional difference.

8. A method in accordance with claim 1 further comprising:
    reconstructing an image of the patient on the table by replacing the second dimension with a sum of the second dimension and the difference;
    reconstructing an additional image from data obtained by scanning at a position displaced N units from a position at which the first set of data is obtained;
    determining an additional difference between the first dimension and a third dimension of the table in the additional image;
    reconstructing another additional image by replacing the third dimension with a sum of the third dimension and the additional difference; and
    correcting at least one difference in images generated from data obtained from positions within the N units by fitting a smooth curve between the additional image and the other additional image.

9. A method in accordance with claim 1 further comprising determining additional differences between additional dimensions from a relationship including the difference between the first dimension and the second dimension of the table in the scanned image.

10. A method in accordance with claim 1 further comprising determining whether the difference can be obtained from an image generated from a scout scan of the patient.

11. An imaging system comprising:
    a source configured to generate energy;
    a table;
    a detector configured to detect the energy; and
    a processor configured to:
        receive a first data set representing a first table position of the table;
        control the source and the detector to scan a patient placed on the table to obtain a second data set at a second table position; and
        determine a difference between a first dimension of the table in the first data se and a corresponding second dimension of the table in the second data set in a scanned image of the table.

12. An imaging system in accordance with claim 11 wherein to control the source and the detector said processor configured to instruct the source and the detector to perform a scout scan of the patient.

13. An imaging system in accordance with claim 11 wherein to control the source and the detector said processor configured to instruct the source and the detector to perform a scan other than a scout scan of the patient.

14. An image system in accordance with claim 11 wherein said processor configured to determine whether the difference can be obtained from an image generated from a scout scan of the patient.

15. A system comprising:
a processor coupled to a detector and configured to:
receive a first data set representing a first table position of a table;
control a source and the detector to scan a patient placed on the table to obtain a second data set at a second table position;
determine a difference between a first dimension of the table in the first data set and a corresponding second dimension of the table in the second data set in a scanned image of the table; and
generate, based on the determined difference, a reconstructed image.

16. A system in accordance with claim 15 wherein to control the source and the detector said processor configured to instruct the source and the detector to perform a scout scan of the patient.

17. A system in accordance with claim 15 wherein to control the source and the detector said processor configured to instruct the source and the detector to perform a scan other than a scout scan of the patient.

18. A method for compensating for table sag, the method comprising:
obtaining a difference between a first dimension of a table in a first data set and a corresponding second dimension of the table in a second data set in an image of the table; and
generating, based on the difference, a reconstructed image comprising dynamically adjusting an isocenter of the reconstructed image based on the difference.

* * * * *